(12) United States Patent
Wang et al.

(10) Patent No.: US 11,049,244 B2
(45) Date of Patent: Jun. 29, 2021

(54) SYSTEMS AND METHODS FOR INTEGRATING TOMOGRAPHIC IMAGE RECONSTRUCTION AND RADIOMICS USING NEURAL NETWORKS

(71) Applicant: Rensselaer Polytechnic Institute, Troy, NY (US)

(72) Inventors: Ge Wang, Loudonville, NY (US); Mannudeep Kalra, Lexington, MA (US); Juergen Hahn, Ballston Lake, NY (US); Uwe Kruger, Ballston Lake, NY (US); Wenxiang Cong, Albany, NY (US); Hongming Shan, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/621,800

(22) PCT Filed: Jun. 18, 2018

(86) PCT No.: PCT/US2018/038040
§ 371 (c)(1),
(2) Date: Dec. 12, 2019

(87) PCT Pub. No.: WO2018/232388
PCT Pub. Date: Dec. 20, 2018

(65) Prior Publication Data
US 2020/0380673 A1    Dec. 3, 2020

Related U.S. Application Data

(60) Provisional application No. 62/520,682, filed on Jun. 16, 2017.

(51) Int. Cl.
*G06T 7/00* (2017.01)
*G06T 7/11* (2017.01)
*G06N 3/08* (2006.01)

(52) U.S. Cl.
CPC .......... *G06T 7/0012* (2013.01); *G06N 3/084* (2013.01); *G06T 7/11* (2017.01);
(Continued)

(58) Field of Classification Search
None
See application file for complete search history.

(56) References Cited

U.S. PATENT DOCUMENTS 9,324,022 B2 *   4/2016  Williams, Jr. ....... G06N 3/0454
2010/0198054 A1   8/2010  Ewing et al.
(Continued)

FOREIGN PATENT DOCUMENTS

| CN | 106372390 A  | 2/2017 |
| CN | 106780460 A  | 5/2017 |
| KR | 101768812 B1 | 8/2017 |

OTHER PUBLICATIONS

Anthimopoulos, Marios, et al. "Lung pattern classification for interstitial lung diseases using a deep convolutional neural network." IEEE transactions on medical imaging 35.5 (2016): 1207-1216. (Year: 2016).*

(Continued)

*Primary Examiner* — Samah A Beg
(74) *Attorney, Agent, or Firm* — Murtha Cullina LLP; Anthony P. Gangemi (57) ABSTRACT

Computed tomography (CT) screening, diagnosis, or another image analysis tasks are performed using one or more networks and/or algorithms to either integrate complementary tomographic image reconstructions and radiomics or map tomographic raw data directly to diagnostic findings in the machine learning framework. One or more reconstruction networks are trained to reconstruct tomographic images from a training set of CT projection data. One or more radiomics networks are trained to extract features from (Continued)

the tomographic images and associated training diagnostic data. The networks/algorithms are integrated into an end-to-end network and trained. A set of tomographic data, e.g., CT projection data, and other relevant information from an individual is input to the end-to-end network, and a potential diagnosis for the individual based on the features extracted by the end-to-end network is produced. The systems and methods can be applied to CT projection data, MRI data, nuclear imaging data, ultrasound signals, optical data, other types of tomographic data, or combinations thereof.

20 Claims, 10 Drawing Sheets

(52) U.S. Cl.
CPC .............. *G06T 2207/10081* (2013.01); *G06T 2207/10088* (2013.01); *G06T 2207/10136* (2013.01); *G06T 2207/20024* (2013.01); *G06T 2207/20081* (2013.01); *G06T 2207/20084* (2013.01); *G06T 2207/20104* (2013.01); *G06T 2207/20182* (2013.01)

(56) References Cited

U.S. PATENT DOCUMENTS

| | | | |
|---|---|---|---|
| 2016/0203599 A1* | 7/2016 | Gillies | G16H 30/40 382/132 |
| 2017/0024634 A1 | 1/2017 | Miao et al. | |
| 2017/0362585 A1* | 12/2017 | Wang | G06N 3/08 |
| 2019/0325621 A1* | 10/2019 | Wang | G06N 3/084 |
| 2019/0328348 A1* | 10/2019 | De Man | G06T 5/40 |
| 2020/0311878 A1* | 10/2020 | Matsuura | G06K 9/4628 |

OTHER PUBLICATIONS

Würfl, Tobias, et al. "Deep learning computed tomography." International conference on medical image computing and computer-assisted intervention. Springer, Cham, 2016. (Year: 2016).*

Caballero, Jose, et al. "Application-driven MRI: joint reconstruction and segmentation from undersampled MRI data." International Conference on Medical Image Computing and Computer-Assisted Intervention. Springer, Cham, 2014. (Year: 2014).*

International Search Report and the Written Opinion of the International Searching Authority, International Application No. PCT/US2018/038040, dated Sep. 6, 2018.

Gruetzemacher, R., et al., "Using Deep Learning for Pulmonary Nodule Detection & Diagnosis," Twenty-second Americas Conference on Information Systems, pp. 1-9, San Diego, 2016.

Cha, K.H., et al., "Bladder Cancer Treatment Response Assessment in CT using Radiomics with Deep-Learning," Scientific Reports, vol. 7, pp. 1-12, Sep. 22, 2016.

Shafiee, M.J., et al., "Discovery Radiomics via Evolutionary Deep Radiomic Sequencer Discovery for Pathologically-Proven Lung Cancer Detection," Computer Science, pp. 1-26, Oct. 20, 2017.

Antropova, N., et al., "Performance comparison of deep learning and segmentation-based radiomic methods in the task of distinguishing benign and malignant breast lesions on DCE-MRI," Proc. of SPIE, vol. 10134, Mar. 3, 2017.

European Search Report, European Patent Application No. EP18817973, dated Feb. 5, 2021.

Caballero, J., et al., "Application-Driven MRI: Joint Reconstruction and Segmentation from Undersampled MRI Data," Advances in Databases and Information Systems, pp. 106-113, Sep. 14, 2014.

* cited by examiner

SYSTEMS AND METHODS FOR INTEGRATING TOMOGRAPHIC IMAGE RECONSTRUCTION AND RADIOMICS USING NEURAL NETWORKS

CROSS REFERENCE TO RELATED APPLICATION(S)

This application claims the benefit of U.S. Provisional Application No. 62/520,682, filed Jun. 16, 2017, which is incorporated by reference as if disclosed herein in its entirety.

BACKGROUND

According to the World Health Organization, cancer is a leading cause of mortality globally with lung cancer alone contributing to 1.69 million deaths in 2015. Lung cancer contributes to nearly one-third cancer-related deaths in the United States. The National Lung Screening Trial (NLST) reported that annual lung cancer screening for three years with low-dose CT (LDCT) resulted in 20% fewer lung cancer related deaths. While this is a positive result, the screenings present major clinical challenges. For example, there is a high frequency of false positive lung nodules on LDCT, and radiologists often have difficulty reliably distinguishing malignant from benign lung nodules, leading to follow-up CT scans and at times invasive (lung biopsy) and expensive (PET-CT) tests. A closely-related challenge is the inaccurate detection of malignant/metastatic potential of indeterminate pulmonary nodules at baseline CT in patients with extra-pulmonary cancers. These cases often require follow-up CT at 3, 6, 9, 12 and 24 months, PET-CT, or tissue biopsy for characterization of these pulmonary nodules. Further, it is projected that LDCT will necessitate a $27.4-billion Medicare budget over a 5-year period, amounting to about $240,000 per additional lung cancer death avoided (assuming a 75% compliance rate to LDCT screening). Relative to digital mammography screening for breast cancer, the cost for LDCT is roughly three-fold higher.

Radiomics has been proposed as a promising method for evaluating lung nodules detected on screening LDCT. The key idea behind the concept of radiomics is that images contain more information than what can be visually perceived, and the hidden information can be extracted. Thus, radiomics has the potential to transform screening LDCT by driving down costs and expedite time to diagnosis of lung cancer, although current radiomic techniques are fundamentally limited.

SUMMARY

Some embodiments of the disclosed subject matter are directed to a system for performing screening, diagnosis, or another image-based analysis tasks. In some embodiments, the system includes a non-transitory computer storage medium coupled with a computer device including one or more processors, the one or more processors configured to execute one or more computer programs encoded on the non-transitory computer storage medium for examining an individual. In some embodiments, the one or more computer programs include a trained end-to-end network, including a reconstruction module including one or more reconstruction algorithms, e.g., filtered backprojection (FBP) type algorithms or iterative compressed sensing algorithms, and/or networks trained to reconstruct tomographic images emphasizing one or more image characteristics, e.g., boundaries, textures, etc., from a set of tomographic data of an individual and a radiomics module integrated with the reconstruction module, the radiomics module including one or more radiomics networks trained to extract features in the tomographic images to diagnostically examine the individual. In some embodiments, the system includes a network training module trained with tomographic training data to map them to associated training diagnostic data, true tomographic sample images, human annotated region of interest segmentation training images, and feature-labeled region of interest training images. In some embodiments, the system maps tomographic training data directly to final diagnostic findings without explicitly involving intermediate images; i.e., bypassing reconstructed images. In some embodiments, the tomographic training data includes CT projection data, MRI data, nuclear imaging data, ultrasound signals, optical data, etc., or combinations thereof.

In some embodiments, the one or more reconstruction networks include a first network trained to reconstruct the tomographic data as a rough image, the first network including a network-based FBP including at least a CNN layer and a backprojection layer, the CNN layer including one or more filters; and a second network trained to refine the rough image and output the tomographic image, the second network including a CNN layer including one or more filters or a sparsely-connected layer, or combinations thereof. In some embodiments, the second network includes a first GAN having a discriminator trained with at least some true tomographic sample images.

In some embodiments, the one or more radiomics networks include a third network trained to identify regions of interest in the tomographic image and output a region of interest segmentation output image, the third network including a CNN layer or a sparsely connected layer, or combinations thereof and a fourth network trained to extract features in the regions of interest and associated diagnostic data to output a feature-extracted tomographic image and identify a potential diagnosis for a set of tomographic data, the fourth network including a fourth CNN layer including one or more filters or a sparsely-connected layer, or combinations thereof. In some embodiments, the third network includes a second GAN having a discriminator trained with at least some human annotated region of interest segmentation training images. In some embodiments, the fourth network includes a third GAN having a third discriminator trained firstly in an unsupervised fashion with region of interest segmentation output images from the third network to remove noise and/or artifacts, and learn to classify based on extracted features, and subsequently in a supervised fashion with the feature-labeled region of interest training images, diagnostic training data, or combinations thereof, to extract features from the regions of interest.

Some embodiments of the disclosed subject matter are directed to a method of performing computed tomography (CT) screening, diagnosis, or another CT-based image analysis tasks. In some embodiments, the method includes providing a training set of CT projection data and associated training diagnostic data from target individuals. In some embodiments, the method includes training one or more reconstruction networks and/or use one or more reconstruction algorithms to reconstruct tomographic images from the training set of CT projection data. In some embodiments, the method includes training one or more radiomics networks to extract features from the tomographic images and the associated training diagnostic data to diagnostically examine the target individuals. In some embodiments, the method includes integrating the one or more reconstruction networks/algorithms and the one or more radiomics networks into an end-to-end network. In some embodiments, the method includes training the end-to-end network. In some embodiments, the method includes inputting at least a set of CT projection data from an individual to the end-to-end network. In some embodiments, the method includes producing a potential diagnosis for the individual based on the features extracted by the end-to-end network.

In some embodiments, the one or more reconstruction networks include a first network trained to reconstruct a rough image from a set of CT projection data and a second network trained to refine the rough image and output the tomographic image. In some embodiments, the first network is a network-based filtered back-projection (FBP) including at least a convolutional neural network (CNN) layer and a backprojection layer, the CNN layer including one or more filters. In some embodiments, the second network includes at least a CNN layer including one or more filters, and a first generative adversarial network (GAN) having a discriminator which determines a loss between the reconstructed tomographic image and a true tomographic sample image.

In some embodiments, the one or more radiomics networks include a third network trained to identify regions of interest in the tomographic image and output a region of interest segmentation output image and a fourth network trained to extract features in the regions of interest and associated diagnostic data to output a feature-extracted tomographic image and identify a potential diagnosis from the set of CT projection data. In some embodiments, wherein the third network includes at least a CNN or sparsely-connected layer, and a second GAN having a discriminator which determines a loss between the region of interest segmentation output image and a human annotated region of interest segmentation training image. In some embodiments, the fourth network includes a CNN layer including one or more filters, and a third GAN having a discriminator which determines a loss between the feature-extracted tomographic image and a feature-labeled region of interest training image. In some embodiments, the fourth network is trained in an unsupervised and/or transfer learning fashion with region of interest segmentation output images to remove noise and/or artifacts, and learn to classify based on extracted features. In some embodiments, the fourth network is fine-tuned in a supervised fashion after the unsupervised training and/or transfer learning.

In some embodiments, the associated training diagnostic data includes pathological results, histological findings, clinical reports, laboratory tests, genetic profiling, genomic assays, proteomic assays, and so on, or combinations thereof.

Some embodiments of the disclosed subject matter are directed to a method of performing CT screening, diagnosis, or another CT-based image analysis tasks which bypasses tomographic image reconstruction to perform "rawdiomics" directly; i.e., end-to-end mapping of raw data to radiomics directly without explicitly involving intermediate images. In some embodiments, the method includes providing a set of tomographic training data and associated training diagnostic data from target individuals, training one or more networks to extract features from the tomographic training data and associated training diagnostic data from target individuals, integrating the one or more networks into a unified end-to-end network, training the unified network with the tomographic training data and the associated training diagnostic data from the target individuals, inputting a set of tomographic data, e.g., raw data, such as an x-ray sonogram, from an individual to the unified end-to-end network, and producing a potential diagnosis for the individual based on the features extracted by the unified end-to-end network.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 2A:
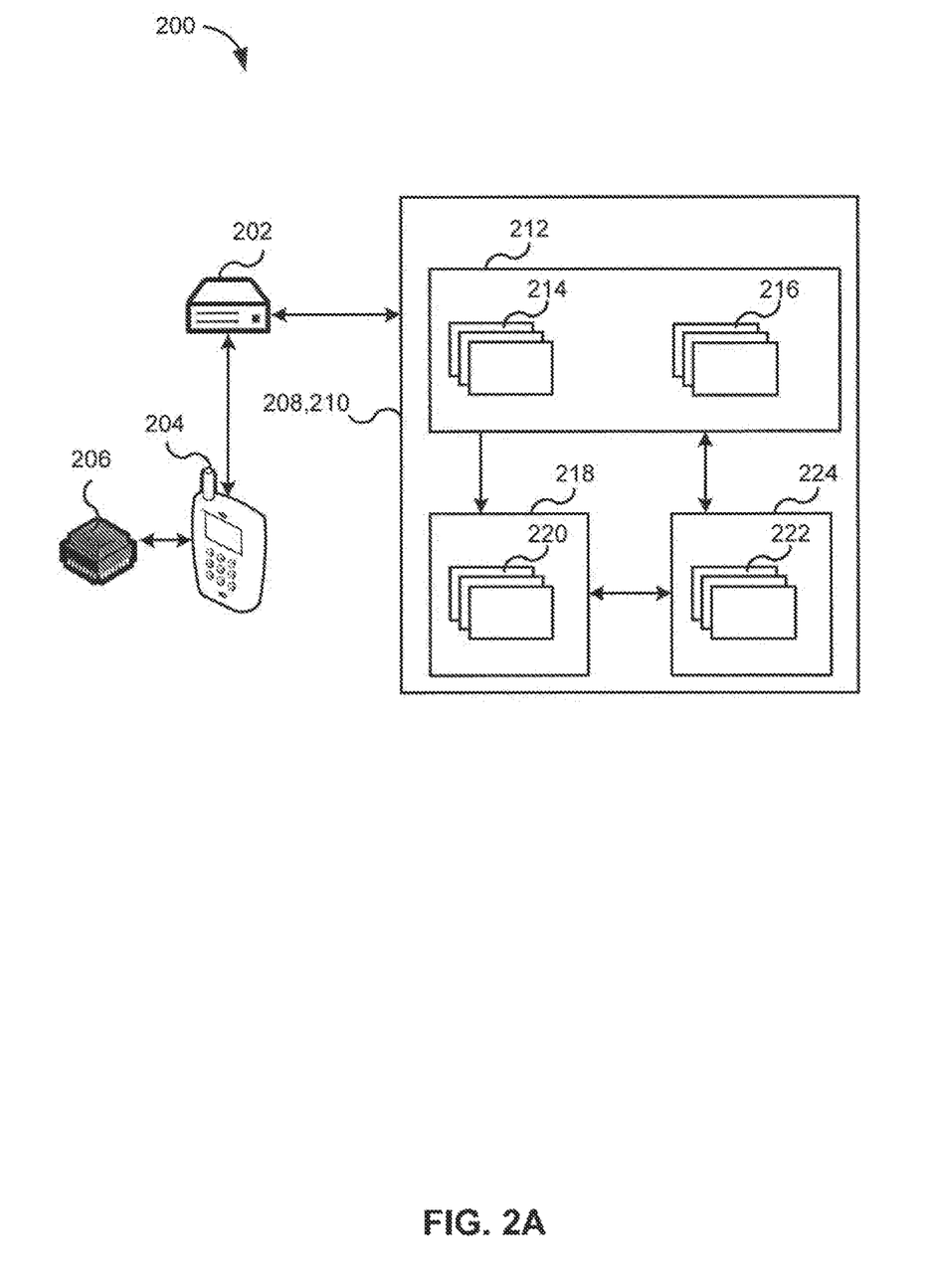
FIG. 2A is a schematic drawing of a system for performing image analysis and radiomics according to some embodiments of the disclosed subject matter.

Referring now to FIG. 2A, aspects of the disclosed subject matter include a system 200 for performing screening, diagnosis, or another image-based analysis tasks related to the examination and/or diagnosis of an individual; e.g., a patient. In some embodiments, the system 200 includes a non-transitory computer storage medium 202 coupled with a computing device 204 including one or more processors 206. The non-transitory computer storage medium 202 can be any suitable storage medium capable of electronically storing data temporarily, permanently, or combinations thereof. The computing device 204 can be any suitable device, e.g., a desktop computer, laptop computer, smart device, etc., for interacting via wired or wireless communication with the data of system 200. The one or more processors 206 are configured to execute one or more computer programs 208 encoded on non-transitory computer storage medium 202.

The one or more computer programs 208 are configured to, alone or in some combination, examine and help diagnose an individual, e.g., for one or more illnesses, conditions, etc. In some embodiments, the one or more computer programs 208 include a network 210, e.g., an artificial neural network (ANN). In some embodiments, network 210 is trained, as will be discussed in greater detail below. The network 210 is described herein as software, however the present disclosure is not limited in this regard, as other configurations are contemplated including where network 210 is operated as a combination of software and hardware or purely as hardware.

In some embodiments, network 210 includes a reconstruction module 212 including one or more reconstruction networks 214, algorithms 216, or combinations thereof. The reconstruction module 212 is trained to reconstruct tomographic images from a set of tomographic data from an individual undergoing examination or screening. In some embodiments, a plurality of different tomographic images are reconstructed from the same training data set, e.g., with the one or more reconstruction networks 214, algorithms 216, or combinations identified above, with the different tomographic images emphasizing one or more image characteristics, e.g., boundaries, textures, etc. The plurality of different tomographic images are then considered in tandem to train the module overall. The tomographic data includes CT projection data, MRI data, nuclear imaging data, ultrasound signals, optical data, etc., or combinations thereof. In some embodiments, network 210 includes a radiomics module 218 including one or more radiomics networks 220. The radiomics module 218 is trained to extract features in tomographic images, e.g., the reconstructed tomographic images from reconstruction module 212, to diagnostically examine an individual undergoing examination or screening. In some embodiments, reconstruction module 212 and radiomics module 218 are integrated as an end-to-end network which advantageously integrates reconstruction of tomographic data to tomographic images, image processing/analysis, and feature extraction, e.g., radiomics, to advantageously provide information for screening, and/or diagnosing an individual based on their own raw tomographic data, associated diagnostic data, or combinations thereof. Exemplary illnesses and/or conditions that can be screened for or diagnosed include, but are not limited to, benign and malignant tumors, cancers, e.g., lung cancers, liver cancers, colon cancers, etc., emphysema, chronic obstructive pulmonary disease (COPD), etc.

In order for network 210 to provide accurate screening, diagnosis, and/or another information processing task, network 210 is trained on a training data set 222 from and representative of a group of target individuals in a population. In some embodiments, the network 210 includes a network training module 224 for training the network 210 on the training data set 222. It is advantageous that the training data set includes as much and representative data as possible and that the data itself be accurate as possible to maximize the quality of the training given to network 210 by training module 224 and thus the reliability of the screening, examination, and/or diagnosis from the network. In some embodiments, the training data set 222 includes, but is not limited to, tomographic training data, e.g., sinograms, associated training diagnostic data, true tomographic sample images, human annotated region of interest segmentation training images, feature-labeled region of interest training images, or combinations thereof. In some embodiments, the tomographic training data includes CT projection data, MRI data, nuclear imaging data, ultrasound signals, optical data, etc., or combinations thereof. In some embodiments, the associated training diagnostic data includes, but is not limited to, pathological results, histological findings, clinical reports, laboratory tests, genetic profiling, genomic assays, proteomic assays, etc., or combinations thereof.

In some embodiments, network training module 224 is configured to train reconstruction module 212 to reconstruct tomographic images from a set of tomographic data from an individual undergoing examination or screening. The framework for system 200 and reconstruction module 212 is, in part, to establish a data-driven relationship from raw data and/or low-quality input images to higher quality output images. Without wishing to be bound by theory, let $X \in R^{m \times n}$ be an input image with noise and artifacts, and $Y \in R^{m \times n}$ be the corresponding ground truth image, with the relationship formulated as Equation 1

$$Y = f(X) \quad (1)$$

where $f: R^{m \times n} \rightarrow R^{m \times n}$ represents the mapping to be learned using reconstruction module 212 through training data set 222 or more generally a prior knowledge library. In some embodiments, this process is formulated as:

$$f = \operatorname*{argmin}_{f} \|f(X) - Y\|_2^2 \quad (2)$$

Reconstruction module 212 is designed to realize Equation 2 as an example (with an exemplary loss function in terms of squared error), as will be described in greater detail below.

In some embodiments, network training module 224 is configured to train radiomics module 218 to extract features in tomographic images to diagnostically examine an individual undergoing examination or screening. In some embodiments, when reconstruction module 212 and radiomics module 218 are integrated as an end-to-end network, network training module 224 is configured to train the end-to-end network from raw data to final diagnosis for performing screening, diagnosis, or another image-based analysis tasks related to the examination and/or diagnosis of an individual, as will be discussed in greater detail below.

Figure 2B:
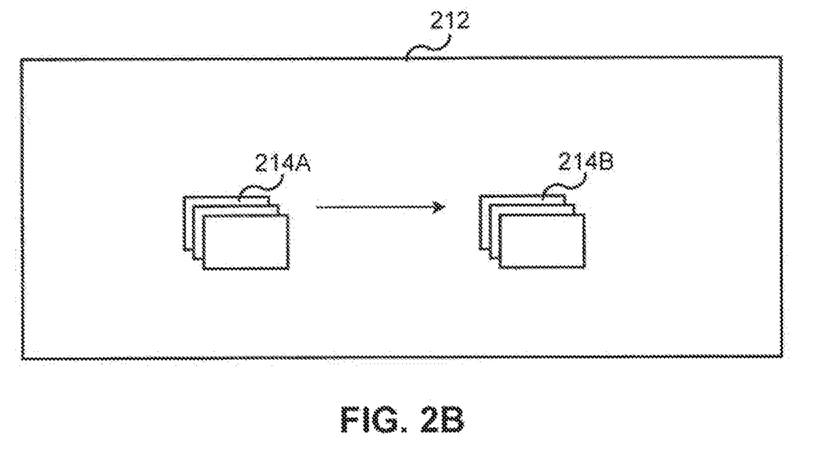
FIG. 2B is a schematic drawing of a network for performing image analysis according to some embodiments of the disclosed subject matter.

Referring now to FIG. 2B, in some embodiments, reconstruction module 212 includes a first network 214A trained to reconstruct one or more rough images from tomographic data, e.g., a set of CT projection data. In some embodiments, first network 214A includes network-based filtered backprojection (FBP) including at least a convolutional neural network (CNN) layer and a backprojection layer. As used herein, CNNs include at least one convolutional layer. In some embodiments, the CNN layer includes one or more filters. In some embodiments, reconstruction module 212 includes a second network 214B trained to refine rough images and output tomographic images. In some embodiments, networks 214A and 214B are combined into a united network to reconstruct images directly. See, for example, H. Chen et al., "LEARN: Learned Experts' Assessment-Based Reconstruction Network for Sparse-Data CT," in IEEE Transactions on Medical Imaging, vol. 37, no. 6, pp. 1333-1347, June 2018, which is incorporated by reference as if disclosed herein in its entirety. In some embodiments, second network 214B includes at least a sparsely-connected layer such as a CNN layer. In some embodiments, the CNN layer includes one or more filters. In some embodiments, second network 214B includes at least a generative adversarial network (GAN). Without wishing to be bound by theory, a GAN includes two components: a generator and a discriminator. The generator aims to provide an output, e.g., a reconstructed image, and the discriminator aims to distinguish between generator outputs and the output's real/true counterparts, i.e., measures a discrepancy between them to make a judgment. In the training of the GAN, the generator and the discriminator compete with each other until the discriminator cannot tell the difference between an artificial output from the generator and a real counterpart. In some embodiments, the second network 214B GAN has a discriminator trained with at least one true tomographic sample image. The second network 214B GAN is trained to differentiate, e.g., determine a discrepancy, between tomographic images, e.g., those reconstructed by networks 214A and/or 214B, and true tomographic sample images.

Figure 2C:
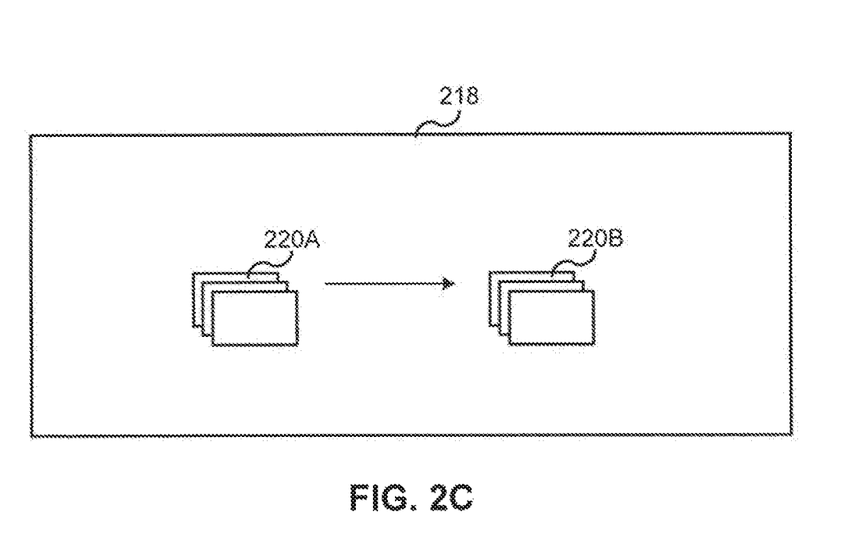
FIG. 2C is a schematic drawing of a network for performing radiomics according to some embodiments of the disclosed subject matter.

Referring now to FIG. 2C, in some embodiments, radiomics module 218 includes a third network 220A trained to identify regions of interest, e.g., around pulmonary nodules, liver masses, or other growths, in tomographic images, and output an image in which the regions of interest are segmented from the background of the image, i.e., as a region of interest segmentation output image. In some embodiments, third network 220A includes at least a sparsely-connected layer such as a CNN layer. In some embodiments, the CNN layer includes one or more filters. In some embodiments, third network 220A includes at least a GAN having a discriminator trained with at least one human annotated region of interest segmentation training image. The third network 220A GAN is trained to differentiate, e.g., determine a discrepancy, between region of interest segmentation output images and human annotated region of interest segmentation training images.

In some embodiments, radiomics module 218 includes a fourth network 220B trained to extract features in regions of interest from region of interest segmentation images, associated diagnostic data, or combinations thereof, and output a feature-extracted tomographic image and/or a potential diagnosis identified for a set of tomographic data. In some embodiments, fourth network 220B includes at least a sparsely-connected layer such as a CNN layer. In some embodiments, the CNN layer includes one or more filters. In some embodiments, fourth network 220B includes at least a GAN having a discriminator. The fourth network 220B GAN is trained to differentiate, e.g., determine a discrepancy, between feature-extracted tomographic images and feature-labeled region of interest training images. In some embodiments, the fourth network 220B is trained in an unsupervised fashion with region of interest segmentation output images from third network 220A to remove noise and/or artifacts, and learn to classify based on extracted features. In some embodiments, the fourth network 220B is trained in a supervised fashion with the feature-labeled region of interest training images, diagnostic training data, or combinations thereof, to extract features from the regions of interest. In some embodiments, the fourth network 220B is trained with transfer-learning. In some embodiments, the training of the fourth network is unsupervised, supervised, via transfer learning, or combinations thereof. In some embodiments, networks 220A and/or 220B is first trained in an unsupervised fashion and subsequently fine-tuned in a supervised fashion. In some embodiments, networks 220A and 220B are combined into a single network and trained together.

Figure 1:
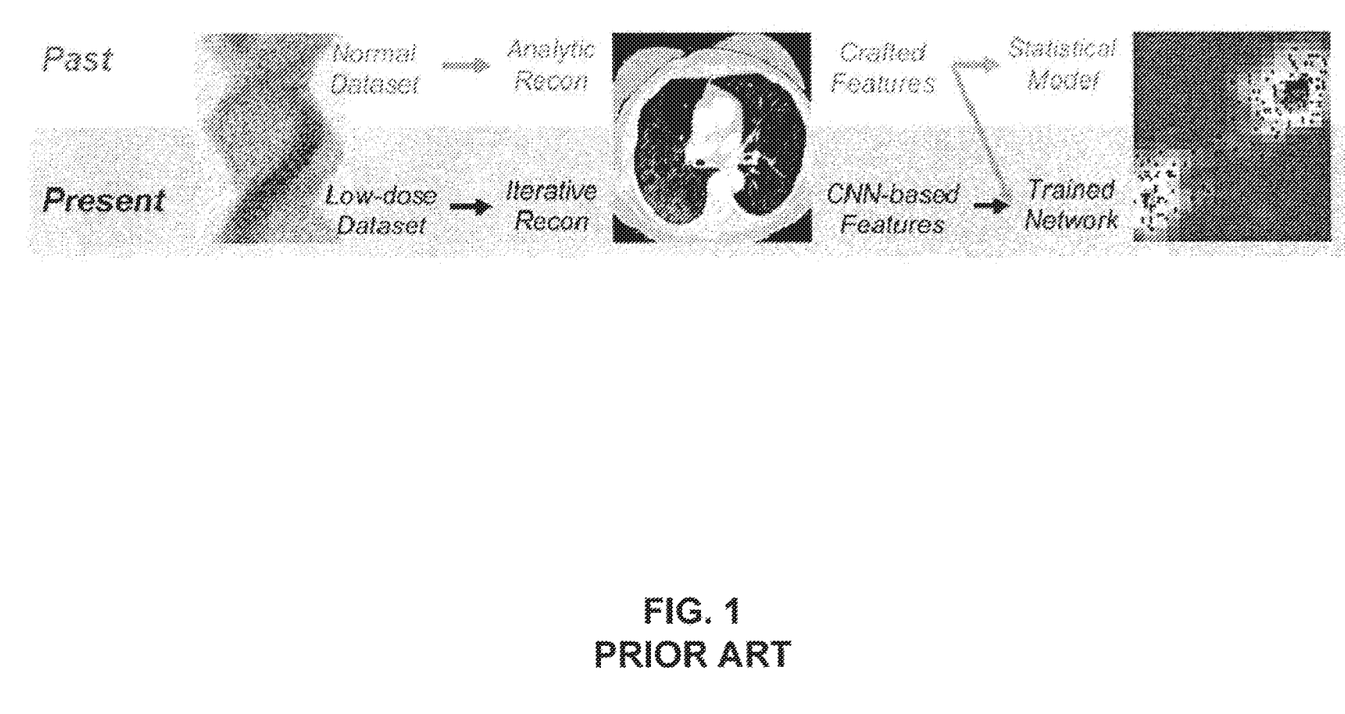
FIG. 1 is a schematic drawing of a workflow for performing image analysis and radiomics according to the prior art.
Figure 3A:
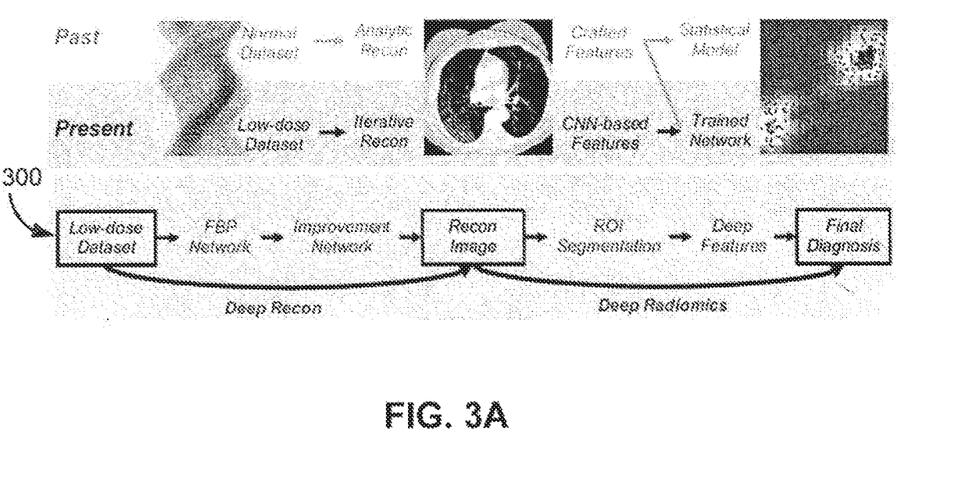
FIG. 3A is a schematic drawing of a workflow for performing image analysis and radiomics according to some embodiments of the disclosed subject matter.
Figure 3B:
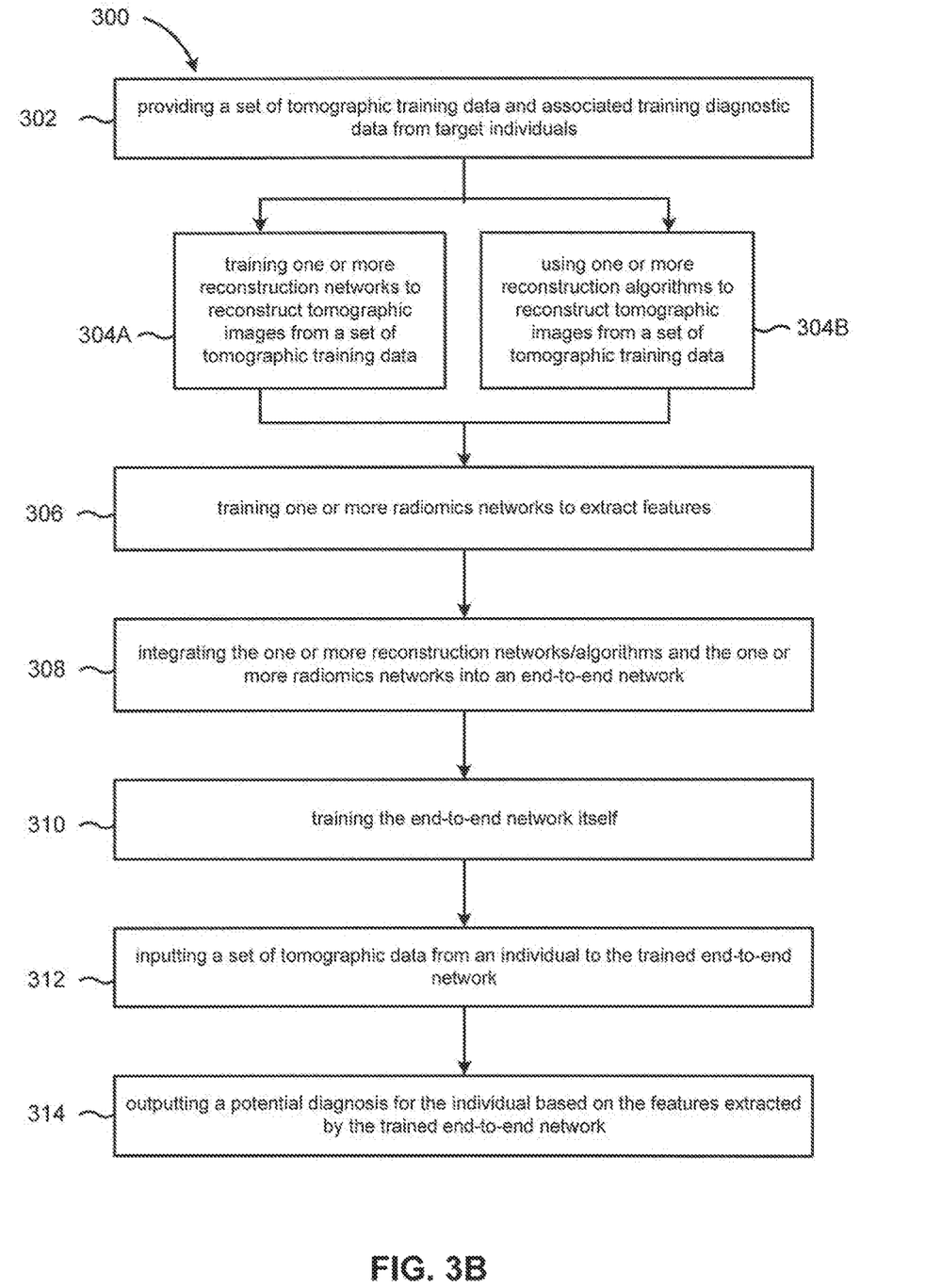
FIG. 3B is a method of performing image analysis and radiomics according to some embodiments of the disclosed subject matter.

Referring now to FIGS. 1, 3A, and 3B, the present disclosure advantageously improves upon the prior art methods of image-based analysis tasks related to the examination and/or diagnosis of an individual. Specifically referring to FIG. 3B, some aspects of the present disclosure are directed to a method 300 of performing screening, diagnosis, or another image-based analysis tasks, e.g., CT screening. In some embodiments of method 300, at 302, a set of tomographic training data and associated training diagnostic data from target individuals are provided. As discussed above, in some embodiments, the set of tomographic training data includes a training set of CT projection data, Mill data, nuclear imaging data, ultrasound signals, optical data, etc., or combinations thereof. In some embodiments, at 304A, one or more reconstruction networks are trained to reconstruct tomographic images from a set of tomographic training data. In some embodiments, at 304B, one or more reconstruction algorithms are used to reconstruct tomographic images from a set of tomographic training data. In some embodiments, method 300 includes both training reconstruction networks 304A and using algorithms 304B.

At 306, one or more radiomics networks are trained to extract features from tomographic images, associated training diagnostic data, or combinations thereof, to diagnostically examine the target individuals. At 308, the one or more reconstruction networks/algorithms and the one or more radiomics networks are integrated into an end-to-end network. In some embodiments, at 310, the end-to-end network itself is trained (together simultaneously or in an alternating fashion), e.g., on the same set of tomographic training data and associated training diagnostic data, or a different set of tomographic training data and associated training diagnostic data, or combinations thereof.

At 312, at least a set of tomographic data from an individual, e.g., CT projection data, is input to the trained end-to-end network. At 314, a potential diagnosis for the individual based on the features extracted by the trained end-to-end network is output.

Figure 4:
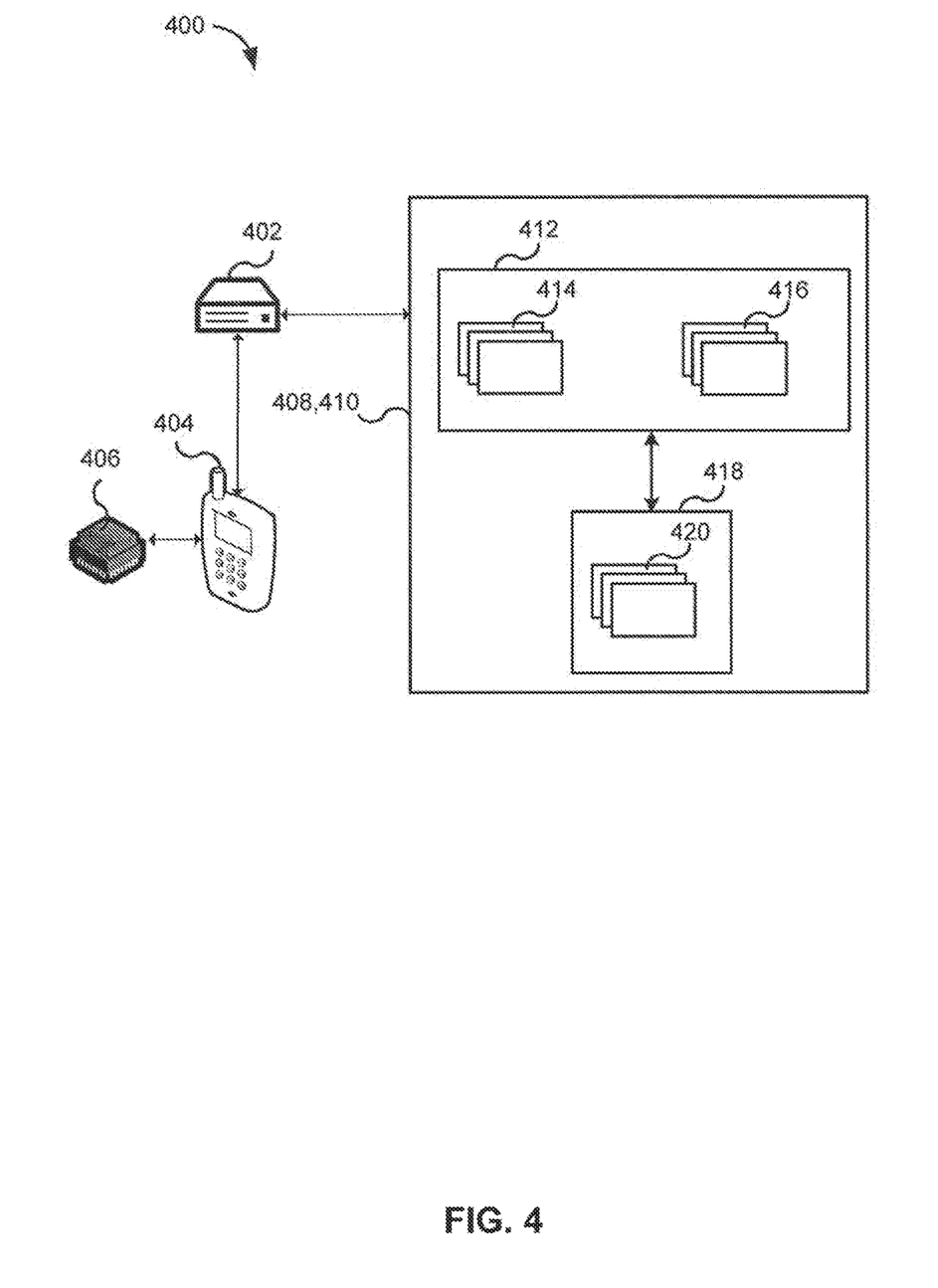
FIG. 4 is a schematic drawing of a system for performing rawdiomics according to some embodiments of the disclosed subject matter.

Referring now to FIG. 4, in some embodiments, the system 200 as described above for screening or diagnosing an individual extracts features and identifies a diagnosis directly from the tomographic data, bypassing explicit tomographic image reconstruction. In these embodiments, referred to herein as system 400, a non-transitory computer storage medium 402 coupled with a computing device 404 including one or more processors 406. The one or more processors 406 are configured to execute one or more computer programs 408 encoded on non-transitory computer storage medium 402.

As with system 200 described above, in system 400 the one or more computer programs 408 are configured to, alone or in some combination, examine and help diagnose an individual, e.g., for one or more illnesses, conditions, etc., via a trained unified end-to-end network 410. In some embodiments, the trained unified end-to-end network 410 includes a radiomics module 412 including one or more networks 414, image processing/analysis algorithms 416, or combinations thereof. In the same manner discussed above with respect to networks 214A, 214B, etc., in system 400 the one or more networks 414 are structured and the radiomics module 412 is trained to extract features directly from the tomographic training data and associated training diagnostic data from target individuals to diagnostically examine the individual.

In some embodiments, the network 410 includes a network training module 418 for training the network 410 on a training data set 420, as described above with respect to network training module 224. In some embodiments, the training data set 420 includes, but is not limited to, tomographic training data and associated training diagnostic data from a population of target individuals. In some embodiments, the tomographic training data includes CT projection data, MRI data, nuclear imaging data, ultrasound signals, optical data, etc., or combinations thereof. In some embodiments, the associated training diagnostic data includes, but is not limited to, pathological results, histological findings, clinical reports, laboratory tests, genetic profiling, genomic assays, proteomic assays, etc., or combinations thereof.

Figure 5A:
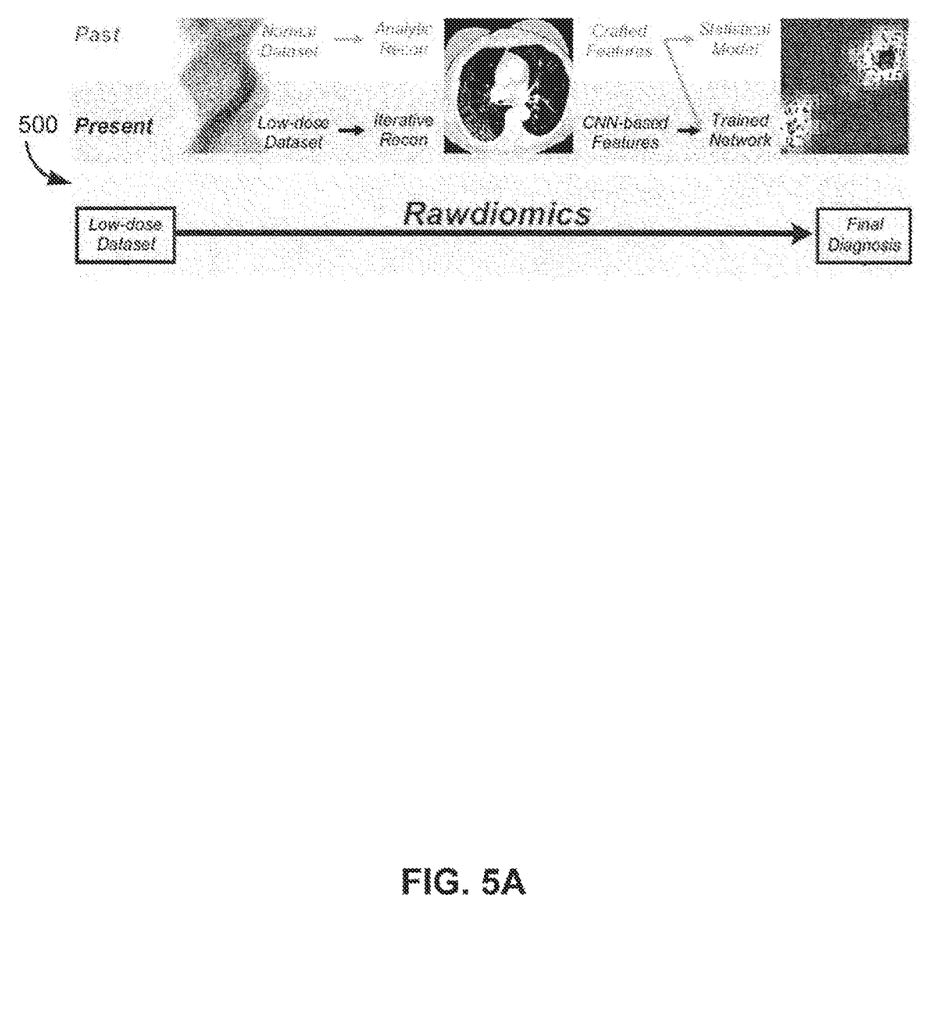
FIG. 5A is a schematic drawing of a workflow for performing rawdiomics according to some embodiments of the disclosed subject matter.
Figure 5B:
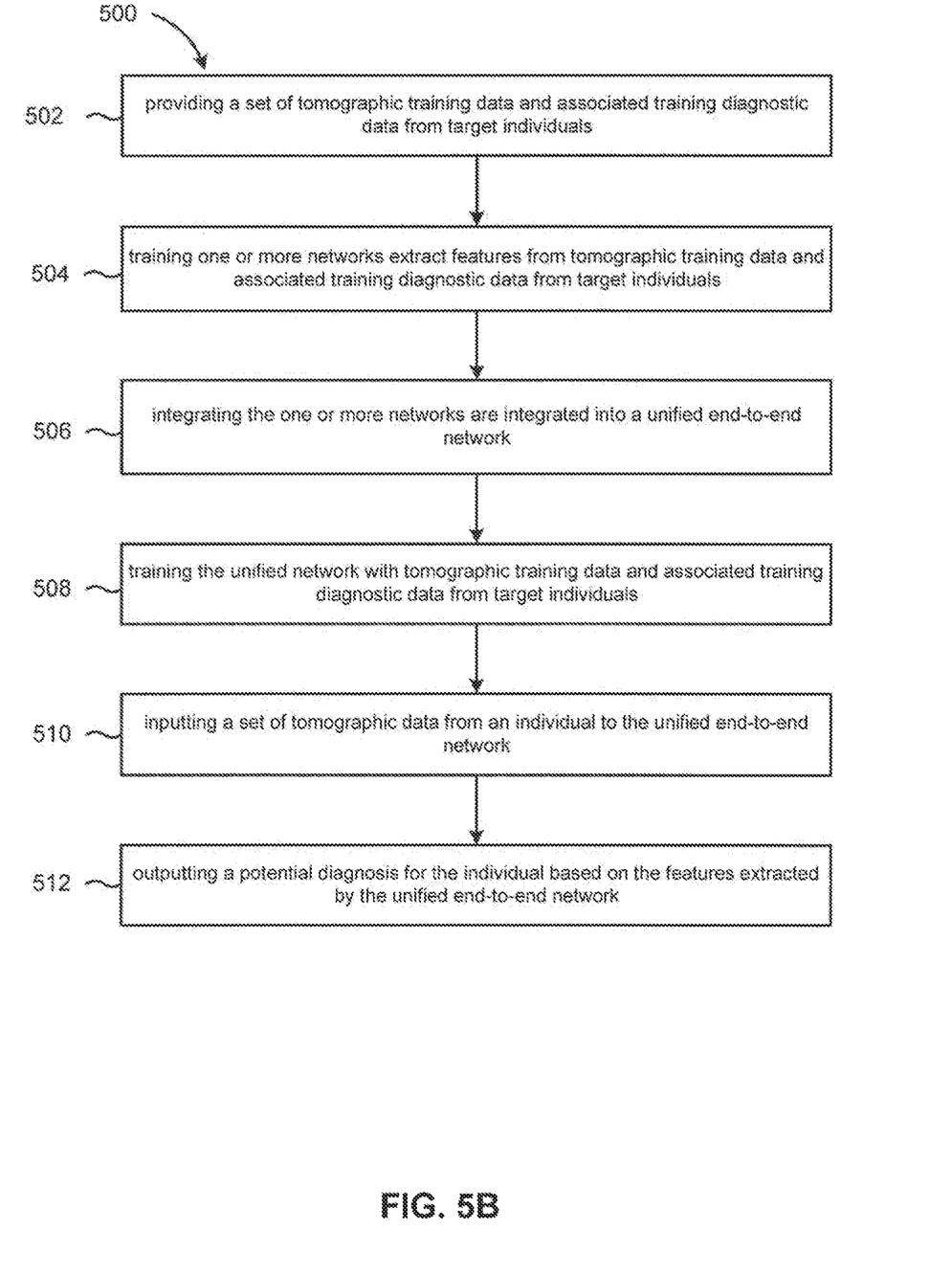
FIG. 5B is a chart of a method of performing rawdiomics according to some embodiments of the disclosed subject matter.

Referring now to FIGS. 1, 5A, and 5B, some aspects of the present disclosure are directed to a method 500 of performing screening, diagnosis, or another image-based analysis task which bypasses tomographic image reconstruction to perform "rawdiomics," i.e., end-to-end mapping of raw data to diagnostic features/findings directly. Specifically referring to FIG. 5B, at 502, a set of tomographic training data and associated training diagnostic data from target individuals are provided. At 504, one or more networks is trained to extract features from tomographic training data and associated training diagnostic data from target individuals, e.g., in a target population. At 506, the one or more networks are integrated into a unified end-to-end network. At 508, the unified network is trained with tomographic training data and associated training diagnostic data from target individuals. At 510, a set of tomographic data from an individual, e.g., a patient, is input to the unified end-to-end network. At 512, a potential diagnosis for the individual is identified based on the features extracted by the unified end-to-end network and output.

Methods and systems of the present disclosure advantageously provide an optimized, holistic workflow for screening, diagnosis, or other image-based analysis tasks related to the examination of an individual. This is featured by a synergistic unification of tomographic reconstruction and radiomics so that the information inherent in raw data can be fully utilized in the machine learning framework. By applying deep learning and related techniques, the system provides comprehensive tomographic reconstructions relative to standard analytic and/or iterative methodologies and large searching space of enriched diagnostically related features. The systems and methods of the present disclosure significantly improve upon the performance of radiomics related tasks, such as region of interest segmentation and feature extraction, which can be tedious, expensive, and relatively unreliable using traditional techniques. Specifically, traditional handcrafted features are often limited to shape-based and texture-based features, while the networks of the present disclosure are capable of extracting millions or even billions of features for greatly improved classification and screening power. Finally, the integrated framework described herein allows for significantly faster, more reliable examination and diagnosis of an individual, even in cases where the only data available is raw tomographic data, i.e., image reconstruction may or may not be explicitly involved for effective diagnosis. Thus, the overall costs of medical care and bias towards over treatment and testing of patients can be minimized by using the systems of the present disclosure to reduce operator inconsistencies and better separate truly at-risk patients from low-risk patients within broadly defined patient populations, e.g., those with a history of colon cancer, liver cancer, and lung cancer, etc., where traditionally all members of that population would be generally treated the same.

Example

Figure 6A:
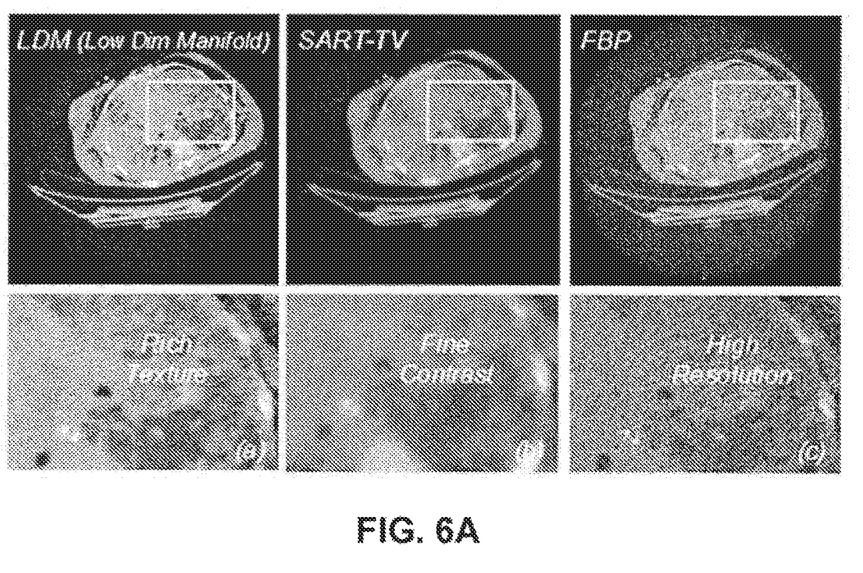
FIG. 6A. is a chart showing differently reconstructed images from the same dataset.
Figure 6B:
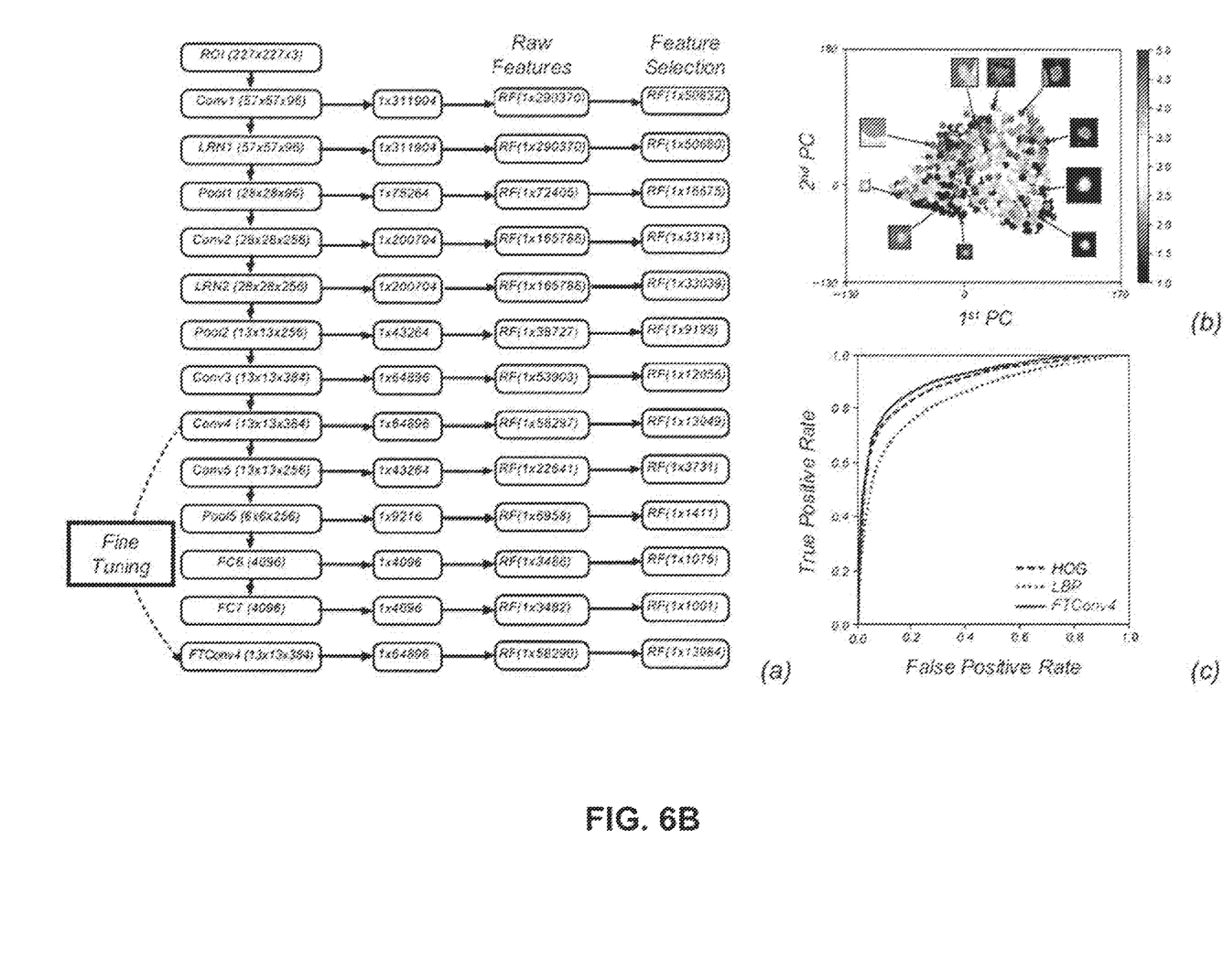
FIG. 6B. is a chart showing extraction of radiomics features using a neural network through transfer learning.

Tomographic image reconstruction of patient tomographic data and radiomic analysis of the reconstructed images were both performed. Referring now to FIG. 6A, CT images from raw patient data were reconstructed using three representative image reconstruction algorithms respectively to highlight features of different types: (a) using a low-dimensional manifold (LDM) based method that we newly developed which reveals rich signatures, (b) using a SART-TV algorithm for fine shading differences, and (c) using an FBP algorithm for high spatial resolution. See, for example, Cong, W., Wang, G., Yang, Q., Hsieh, J., Li, J., & Lai, R. (2017). CT Image Reconstruction in a Low Dimensional Manifold. CoRR, abs/1704.04825 which is incorporated by reference as if disclosed herein in its entirety. Referring now to FIG. 6B, portraying CNN-based classification of lung nodules: (a) The network structure for feature extraction from the pre-trained AlexNet after fine-tuning and feature selection, (b) learned features visualized in a 2D space with the horizontal and vertical axes for the first two principal components (PCs) to separate malignant (red) and benign (blue) samples, and (c) our proposed method FTCov4 achieves a better performance than the state-of-the-art texture descriptors, e.g., histogram of oriented gradients (HOG) and local binary patterns (LBP). See, for example, Shan H, Wang G, Kalra M K, de Souza R, Zhang J: Enhancing Transferability of Features from Pretrained Deep Neural Networks for Lung Nodule Classification. In: The Proceedings of the 2017 International Conference on Fully Three-Dimensional Image Reconstruction in Radiology and Nuclear Medicine (Fully3D), Xi'an, China; 2017, which is incorporated by reference as if disclosed herein in its entirety. This example shows the potential and power of the rawdiomics systems and methods described in the present disclosure, namely that a patient population which formerly would have received uniform treatment, e.g., the same frequency of check-ups, preventative screenings, etc., can now be better segmented so that time and resources can be devoted proportionally to patients more at risk for metastasis, while those patients at lower risk of metastasis are not subjected to arguably unnecessary treatment.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of performing computed tomography (CT) screening, diagnosis, or another CT-based image analysis tasks, comprising:
   providing a training set of CT projection data and associated training diagnostic data from target individuals;
   training one or more reconstruction networks to reconstruct tomographic images from the training set of CT projection data;
   training one or more radiomics networks to extract features from the tomographic images and the associated training diagnostic data to diagnostically examine the target individuals;
   integrating the one or more reconstruction networks and the one or more radiomics networks into an end-to-end network;
   training the end-to-end network;
   inputting at least a set of CT projection data from an individual to the end-to-end network; and
   producing a potential diagnosis for the individual based on the features extracted by the end-to-end network.

2. The method according to claim 1, wherein the one or more reconstruction networks include:
   a first network trained to reconstruct the set of CT projection data as a rough image; and
   a second network trained to refine the rough image and output the tomographic image.

3. The method according to claim 2, wherein the first network is a network-based filtered back-projection (FBP)

including at least a convolutional neural network (CNN) layer and a backprojection layer, the CNN layer including one or more filters.

4. The method according to claim 2, wherein the second network includes at least a CNN layer including one or more filters, and a first generative adversarial network (GAN) having a discriminator which determines a loss between the reconstructed tomographic image and a true tomographic sample image.

5. The method according to claim 1, wherein the one or more radiomics networks include:
a third network trained to identify regions of interest in the tomographic image and output a region of interest segmentation output image; and
a fourth network trained to extract features in the regions of interest and associated diagnostic data to output a feature-extracted tomographic image and identify a potential diagnosis from the set of CT projection data.

6. The method according to claim 5, wherein the third network includes at least a CNN and a second GAN having a discriminator which determines a loss between the region of interest segmentation output image and a human annotated region of interest segmentation training image.

7. The method according to claim 5, wherein the fourth network includes a CNN layer including one or more filters, and a third GAN having a discriminator which determines a loss between the feature-extracted tomographic image and a feature-labeled region of interest training image.

8. The method according to claim 7, wherein the fourth network is trained in an unsupervised fashion with region of interest segmentation output images to remove noise and/or artifacts, and learn to classify based on extracted features, via transfer learning, or combinations thereof.

9. The method according to claim 8, wherein the fourth network is fine-tuned in a supervised fashion after the unsupervised training, transfer learning, or combinations thereof.

10. The method according to claim 1, wherein the associated training diagnostic data includes pathological results, histological findings, clinical reports, laboratory tests, genetic profiling, genomic assays, proteomic assays, or combinations thereof.

11. A system for performing screening, diagnosis, or another image-based analysis tasks, comprising:
a non-transitory computer storage medium coupled with a computer device including one or more processors, the one or more processors configured to execute one or more computer programs encoded on the non-transitory computer storage medium for examining an individual, the one or more computer programs including:
a trained end-to-end network, including:
a reconstruction module including one or more reconstruction algorithms and/or networks trained to reconstruct tomographic images from a set of tomographic data from the individual; and
a radiomics module integrated with the reconstruction module, the radiomics module including one or more radiomics networks trained to extract features in the tomographic images to diagnostically examine the individual.

12. The system according to claim 11, further comprising a network training module including tomographic training data, associated training diagnostic data, true tomographic sample images, human annotated region of interest segmentation training images, and feature-labeled region of interest training images.

13. The system according to claim 12, wherein the one or more reconstruction networks include:
a first network trained to reconstruct the tomographic data as a rough image, the first network including a network-based FBP including at least a CNN layer and a backprojection layer; and
a second network trained to refine the rough image and output the tomographic image, the second network including at least a CNN layer or a sparsely-connected layer.

14. The system according to claim 12, wherein the one or more radiomics networks include:
a third network trained to identify regions of interest in the tomographic image and output a region of interest segmentation output image, the third network including at least a CNN layer or a sparsely connected layer; and
a fourth network trained to extract features in the regions of interest and associated diagnostic data to output a feature-extracted tomographic image and identify a potential diagnosis for a set of tomographic data, the fourth network including at least a CNN layer or a sparsely-connected layer.

15. The system according to claim 13, wherein the second network includes a GAN trained with at least some true tomographic sample images.

16. The system according to claim 14, wherein the third network includes a GAN trained with at least some human annotated region of interest segmentation training images.

17. The system according to claim 14, wherein the fourth network includes a GAN trained firstly in an unsupervised fashion with region of interest segmentation output images from the third network to remove noise and/or artifacts, and learn to classify based on extracted features, and subsequently in a supervised fashion with the feature-labeled region of interest training images, diagnostic training data, or combinations thereof, to extract features from the regions of interest.

18. The method according to claim 12, wherein the tomographic training data includes CT projection data, MRI data, nuclear imaging data, ultrasound signals, optical data, or combinations thereof.

19. A method of performing screening, diagnosis, or another image-based analysis tasks, comprising:
providing a set of tomographic training data and associated training diagnostic data from target individuals;
training one or more networks to extract features from the tomographic training data and associated training diagnostic data from target individuals;
integrating the one or more networks into a unified end-to-end network;
training the unified network with the tomographic training data and the associated training diagnostic data from the target individuals;
inputting a set of tomographic data from an individual to the unified end-to-end network; and
producing a potential diagnosis for the individual based on the features extracted by the unified end-to-end network.

20. The method according to claim 19, wherein the tomographic training data includes CT projection data, Mill data, nuclear imaging data, ultrasound signals, optical data, or combinations thereof.

* * * * *